US010403262B2

(12) United States Patent
Tani

(10) Patent No.: US 10,403,262 B2
(45) Date of Patent: Sep. 3, 2019

(54) ACTIVE NOISE CONTROL DEVICE, CAR, AND ACTIVE NOISE CONTROL METHOD

(71) Applicant: PANASONIC INTELLECTUAL PROPERTY MANAGEMENT CO., LTD., Osaka (JP)

(72) Inventor: Mitsuhiro Tani, Osaka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 0 days.

(21) Appl. No.: 16/166,402

(22) Filed: Oct. 22, 2018

(65) Prior Publication Data

US 2019/0130890 A1 May 2, 2019

(30) Foreign Application Priority Data

Oct. 27, 2017 (JP) ................................ 2017-208492

(51) Int. Cl.

| | |
|---|---|
| ***G10K 11/16*** | (2006.01) |
| ***H03B 29/00*** | (2006.01) |
| ***A61F 11/06*** | (2006.01) |
| ***G10K 11/178*** | (2006.01) |

(52) U.S. Cl.

CPC .. *G10K 11/17835* (2018.01); *G10K 11/17823* (2018.01); *G10K 2210/1282* (2013.01)

(58) Field of Classification Search

CPC ............... G10K 11/175; G10K 11/178; G10K 11/1781; G10K 11/17815; G10K 11/17821; G10K 11/17823; G10K 11/17835; G10K 11/17837; G10K 11/17854; G10K 11/17879; G10K 11/17881; G10K 2201/128; G10K 2201/1281; G10K 2201/1282; G10K 2201/1283

USPC ........ 381/71.1, 71.2, 71.4, 71.8, 71.9, 71.11, 381/71.14, 86, 94.1–94.8

See application file for complete search history.

(56) References Cited

U.S. PATENT DOCUMENTS

| | | | | |
|---|---|---|---|---|
| 5,319,715 A * | 6/1994 | Nagami | G10K 11/178 | 381/71.14 |
| 7,873,173 B2 * | 1/2011 | Inoue | G10K 11/1784 | 331/10 |
| 8,036,396 B2 * | 10/2011 | Sakamoto | G10K 11/178 | 381/71.4 |
| 8,098,836 B2 * | 1/2012 | Sakamoto | G10K 11/178 | 381/71.4 |
| 9,445,192 B2 * | 9/2016 | Ueno | G10K 11/178 | |
| 9,691,373 B2 * | 6/2017 | Kano | G10K 11/178 | |
| 10,276,146 B2 * | 4/2019 | Hiraga | B60R 11/02 | |

(Continued)

FOREIGN PATENT DOCUMENTS

| | | |
|---|---|---|
| JP | 3499574 | 3/1993 |
| JP | 06-230789 | 8/1994 |

(Continued)

*Primary Examiner* — Xu Mei

(74) *Attorney, Agent, or Firm* — Greenblum & Bernstein, P.L.C.

(57) ABSTRACT

An active noise control device reduces noise inside a cabin of a car. The active noise control device includes: a controller that decreases a signal level of a canceling signal when a signal level of a received reference signal is lower than a threshold; and a threshold controller that changes the threshold based on at least one of a signal level of an error signal and information on the car.

18 Claims, 9 Drawing Sheets

(56) References Cited

U.S. PATENT DOCUMENTS

| | | | | |
|---|---|---|---|---|
| 2015/0063581 A1* | 3/2015 | Tani | G10K 11/178 | 381/71.2 |
| 2015/0104030 A1* | 4/2015 | Ueno | G10K 11/178 | 381/71.4 |
| 2015/0356965 A1 | 12/2015 | Tani et al. | | |

FOREIGN PATENT DOCUMENTS

| | | |
|---|---|---|
| JP | 4004710 | 10/2001 |
| WO | 2014/115533 | 7/2014 |

* cited by examiner

ACTIVE NOISE CONTROL DEVICE, CAR, AND ACTIVE NOISE CONTROL METHOD

CROSS REFERENCE TO RELATED APPLICATION

The present application claims the benefit of Japanese Patent Application No. 2017-208492 filed Oct. 27, 2017. The entire disclosure of the above-identified application, including the specification, drawings and claims is incorporated herein by reference in its entirety.

FIELD

The present disclosure relates to an active noise control device, a car including this device, and an active noise control method which actively reduce noise by producing interference between the noise and a canceling sound.

BACKGROUND

Conventionally, an active noise control device has been known which actively reduces noise by emitting a canceling sound for canceling the noise from a canceling sound source using a reference signal having correlation with the noise and an error signal corresponding to a residual sound resulting from interference between the canceling sound and the noise in a predetermined space (see Patent Literature 1, for example). The active noise control device generates the canceling signal for emitting the canceling sound, using an adaptive filter in such a manner that the sum of squares of the error signal is minimized.

CITATION LIST

Patent Literature

[PTL 1] Japanese Patent No. 3499574

SUMMARY

Technical Problem

However, the foregoing active noise control device according to PTL 1 can be improved upon. In view of this, the present disclosure provides a noise control device, a car, and a noise control method which can achieve further improvements.

Solution to Problem

An active noise control device according to an aspect of the present disclosure is an active noise control device that reduces noise inside a cabin of a car, the active noise control device including: a reference signal input unit that receives a reference signal having correlation with the noise; an adaptive filter unit that generates a canceling signal by applying an adaptive filter to the reference signal received; a canceling signal output unit that receives the canceling signal generated; an error signal input unit that receives an error signal corresponding to a residual sound resulting from interference between the noise and a canceling sound emitted from a canceling sound source according to the canceling signal; a simulated acoustic transfer characteristic filter unit that generates a filtered reference signal by adjusting the reference signal using simulated transfer characteristics which simulate acoustic transfer characteristics from the canceling signal output unit to the error signal input unit; a filter coefficient updater that sequentially updates a coefficient of the adaptive filter using the error signal and the filtered reference signal generated; a controller that decreases a signal level of the canceling signal when a signal level of the reference signal received is lower than a threshold; and a threshold controller that changes the threshold based on at least one of a signal level of the error signal and information on the car.

An active noise control device according to an aspect of the present disclosure is an active noise control device that reduces noise inside a cabin of a car, the active noise control device including: a reference signal input unit that receives a reference signal having correlation with the noise; an adaptive filter unit that generates a canceling signal by applying an adaptive filter to the reference signal received; a canceling signal output unit that receives the canceling signal generated; an error signal input unit that receives an error signal corresponding to a residual sound resulting from interference between the noise and a canceling sound emitted from a canceling sound source according to the canceling signal; a simulated acoustic transfer characteristic filter unit that generates a filtered reference signal by adjusting the reference signal using simulated transfer characteristics which simulate acoustic transfer characteristics from the canceling signal output unit to the error signal input unit; a filter coefficient updater that sequentially updates a coefficient of the adaptive filter using the error signal and the filtered reference signal generated; a car information input unit that receives information on the car; a controller that decreases a signal level of the canceling signal when a first parameter included in the information on the car is lower than a threshold; and a threshold controller that changes the threshold based on at least one of a signal level of the error signal and a second parameter included in the information on the car, the second parameter being different from the first parameter.

A car according to an aspect of the present disclosure includes the active noise control device, and the canceling sound source.

An active noise control method according to an aspect of the present disclosure is an active noise control method for reducing noise inside a cabin of a car, the active noise control method including: generating a canceling signal by applying an adaptive filter to a reference signal having correlation with the noise; generating a filtered reference signal by adjusting the reference signal using simulated transfer characteristics which simulate acoustic transfer characteristics from a canceling signal output unit to an error signal input unit, the canceling signal output unit receiving the canceling signal, the error signal input unit receiving an error signal corresponding to a residual sound resulting from interference between the noise and a canceling sound emitted from a canceling sound source according to the canceling signal generated; sequentially updating a coefficient of the adaptive filter using the error signal and the filtered reference signal generated; decreasing a signal level of the canceling signal when a signal level of the reference signal received is lower than a threshold; and changing the threshold based on at least one of a signal level of the error signal and information on the car.

An active noise control method according to an aspect of the present disclosure is an active noise control method for reducing noise inside a cabin of a car, the active noise control method including: generating a canceling signal by applying an adaptive filter to a reference signal having correlation with the noise; generating a filtered reference signal by adjusting the reference signal using simulated transfer characteristics which simulate acoustic transfer characteristics from a canceling signal output unit to an error signal input unit, the canceling signal output unit receiving the canceling signal, the error signal input unit receiving an error signal corresponding to a residual sound resulting from interference between the noise and a canceling sound emitted from a canceling sound source according to the canceling signal generated; sequentially updating a coefficient of the adaptive filter using the error signal and the filtered reference signal generated; decreasing a signal level of the canceling signal when a first parameter included in information on the car is lower than a threshold; and changing the threshold based on at least one of a signal level of the error signal and a second parameter included in the information on the car, the second parameter being different from the first parameter.

Advantageous Effects

The active noise control device, etc. according to the present disclosure can achieve further improvements.

These and other objects, advantages and features of the present disclosure will become apparent from the following description thereof taken in conjunction with the accompanying drawings that illustrate a specific embodiment of the present disclosure.

DESCRIPTION OF EMBODIMENT

Hereinafter, embodiments will specifically be described with reference to the drawings. The embodiments described below each illustrate a general or particular example of the present disclosure. Thus, the numerical values, shapes, materials, elements, the arrangement and connection of the elements, steps, the order of the steps, etc., indicated in the following embodiments are mere examples, and are not intended to limit the present disclosure. Therefore, among the elements in the following embodiments, elements not recited in any of the independent claims defining the most generic concept of the present disclosure are described as optional elements.

Furthermore, the drawings are schematic and do not necessarily provide precise depictions. Throughout the drawings, like elements share like reference signs and redundant description is omitted or simplified.

Embodiment 1

[Configuration of Car Including Active Noise Control Device]

Figure 1:
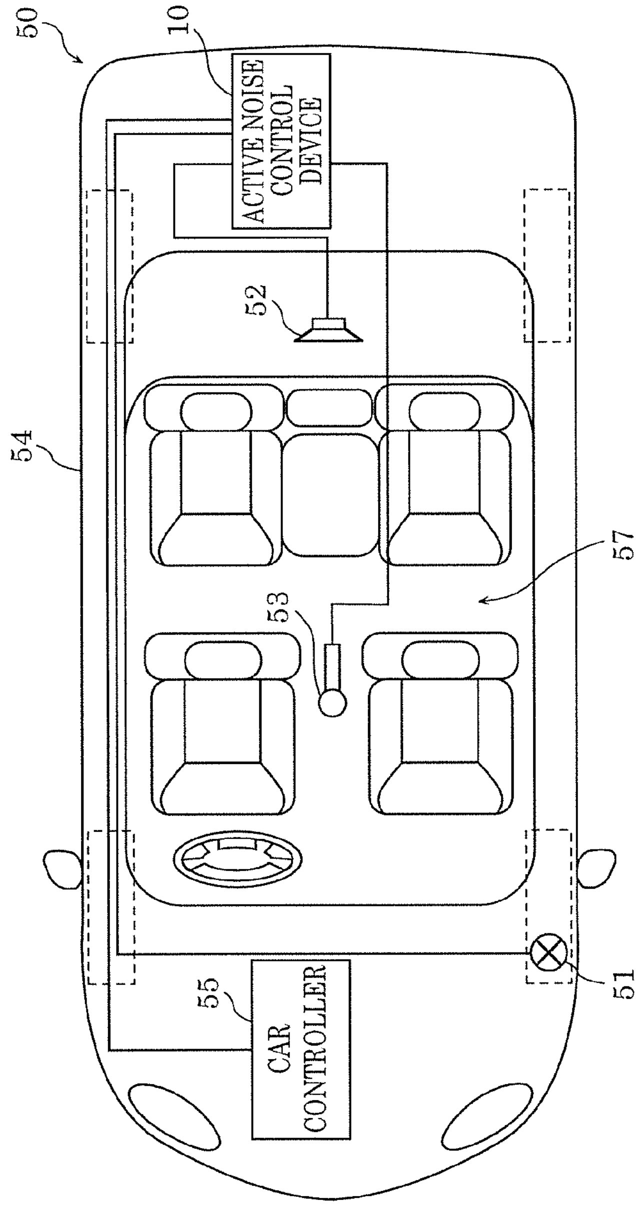
FIG. 1 is a schematic top view illustrating a car including an active noise control device according to embodiment 1.

Embodiment 1 describes an active noise control device for use in a car. FIG. 1 is a schematic top view illustrating a car including an active noise control device according to embodiment 1.

Car 50 is an example of a vehicle, and includes active noise control device 10 according to embodiment 1, reference signal source 51, canceling sound source 52, error signal source 53, car body 54, and car controller 55. Specifically, car 50 is an automobile, but not limited to this.

Reference signal source 51 is a transducer which provides a reference signal having correlation with noise in space 57 of a cabin of car 50. In embodiment 1, reference signal source 51 is an acceleration sensor which is disposed outside space 57. Specifically, reference signal source 51 is mounted on a sub frame. It should be noted that reference signal source 51 may be mounted on any other position.

Canceling sound source 52 emits a canceling sound to space 57 using a canceling signal. In embodiment 1, canceling sound source 52 is a speaker. However, the canceling sound may be emitted by exciting a component structure of car 50 (for example, a sun roof, etc.) using drive mechanism such as an actuator. Furthermore, two or more canceling sound sources 52 may be used in active noise control device 10, and the positions of canceling sound sources 52 are not particularly limited.

Error signal source 53 detects a residual sound resulting from interference between the noise and the canceling sound in space 57, and provides an error signal based on the residual sound. Error signal source 53 is a transducer such as a micro phone, which is preferably installed in space 57. It should be noted that car 50 may include two or more error signal sources 53.

Car body 54 is a structure including a chassis and a body of car 50. Car body 54 forms space 57 (a cabin space) in which canceling sound source 52 and error signal source 53 are disposed.

Car controller 55 controls (drives) car 50 based on the operation of a driver in car 50. Furthermore, car controller 55 provides information on car 50. For example, the information on car 50 is information indicating a driving state of car 50. However, the information on car 50 may be information indicating a state of equipment in the car. For example, car controller 55 is an Electronic control unit (ECU). Specifically, car controller 55 is implemented as a processor, a microcomputer, a dedicated circuit, or the like. Car controller 55 may be implemented in a combination of at least two of a processor, a microcomputer, and a dedicated circuit.

[Configuration of Active Noise Control Device]

Figure 2:
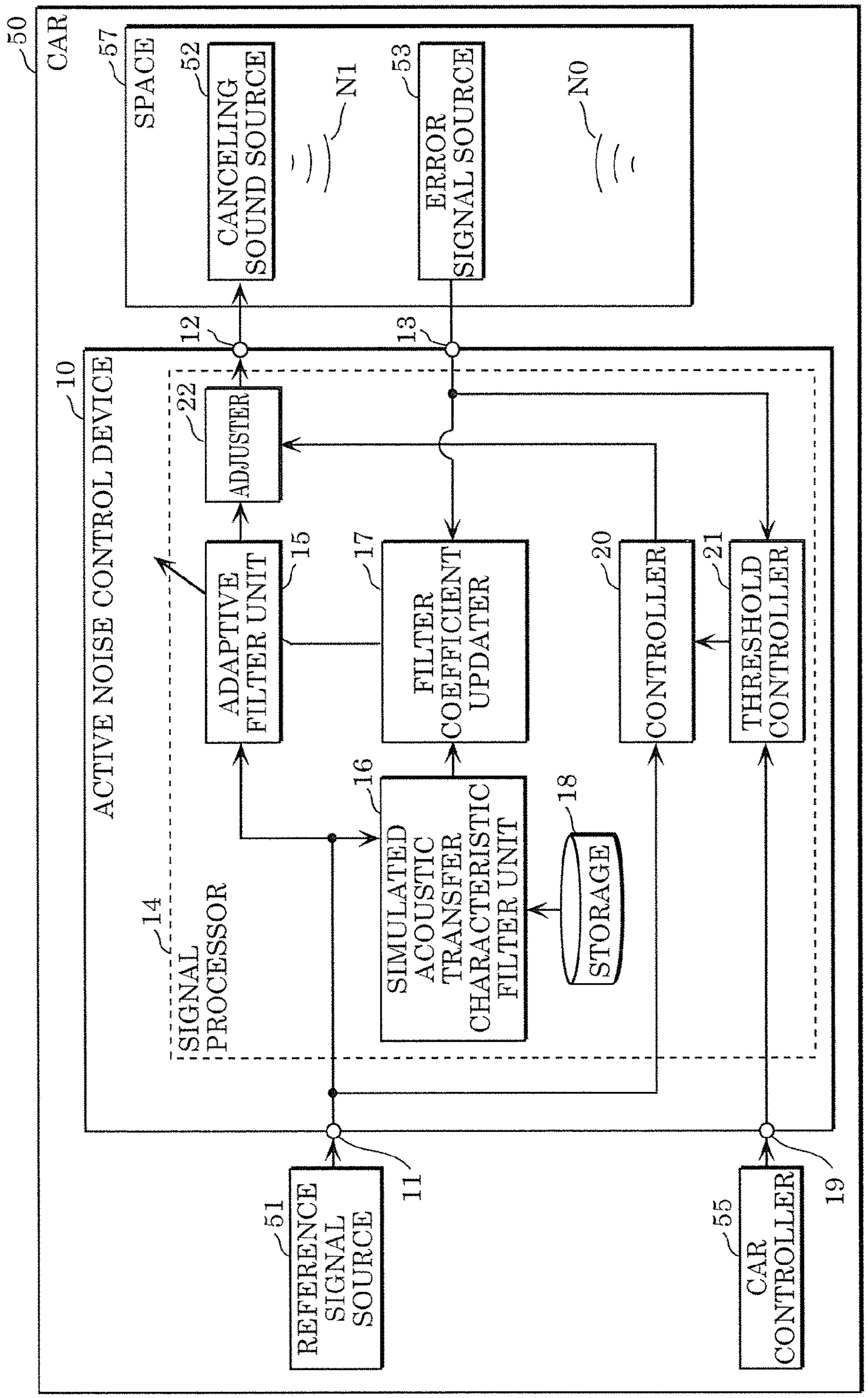
FIG. 2 is a block diagram illustrating the functional configuration of the active noise control device according to embodiment 1.

Next, the configuration of active noise control device 10 will be described. FIG. 2 is a block diagram illustrating the functional configuration of active noise control device 10.

As shown in FIG. 2, active noise control device 10 includes reference signal input terminal 11, canceling signal output terminal 12, error signal input terminal 13, signal processor 14, and car information input terminal 19. Signal processor 14 includes adaptive filter unit 15, simulated acoustic transfer characteristic filter unit 16, filter coefficient updater 17, storage 18, controller 20, threshold controller 21, and adjuster 22. For example, signal processor 14 is implemented as a processor such as a digital signal processor (DSP), but may be implemented as a microcomputer, a dedicated circuit, or a combination thereof. Furthermore, storage 18 may be separated from signal processor 14. Elements in signal processor 14 other than storage 18 also may be separated from signal processor 14.

[Basic Operation]

Figure 3:
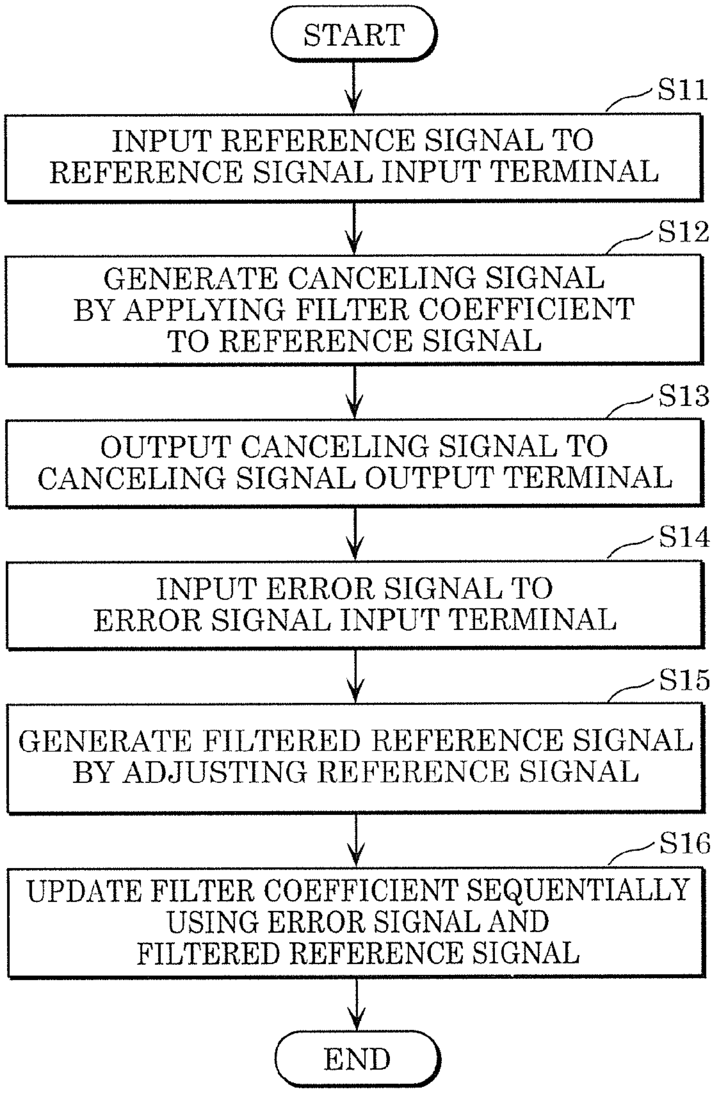
FIG. 3 is a flow chart illustrating the basic operation of the active noise control device according to embodiment 1.

As described above, active noise control device 10 performs a noise reduction operation. Firstly, the basic operation of active noise control device 10 will be described with reference to FIG. 3 as well as FIG. 2. FIG. 3 is a flow chart illustrating the basic operation of active noise control device 10.

First, a reference signal having correlation with noise N0 is inputted from reference signal source 51 to reference signal input terminal 11 (S11). Reference signal input terminal 11 is an exemplary input unit, particularly a terminal formed by metal, etc.

Next, signal processor 14 generates a canceling signal to be used to emit canceling sound N1 for reducing noise N0, by using the reference signal inputted to reference signal input terminal 11. Specifically, adaptive filter unit 15 in signal processor 14 generates the canceling signal by applying (multiplying) an adaptive filter to (by) the reference signal inputted to reference signal input terminal 11 (S12). Adaptive filter unit 15 is implemented as a so-called FIR filter or IIR filter. Adaptive filter unit 15 outputs the generated canceling signal to canceling signal output terminal 12. The canceling signal is used to emit canceling sound N1 for reducing noise N0, and is outputted to canceling signal output terminal 12 (S13).

Canceling signal output terminal 12 is an exemplary canceling signal output unit, particularly a terminal formed by metal, etc. Canceling signal output terminal 12 receives the canceling signal generated by adaptive filter unit 15. It should be noted that adjuster 22 is located between adaptive filter unit 15 and canceling signal output terminal 12. Adjuster 22 is an element for multiplying the canceling signal by a level adjustment factor $\alpha$ in an abnormal sound suppression operation described below, and in the basic operation, the level adjustment factor is $\alpha=1$.

Canceling signal output terminal 12 is connected to canceling sound source 52. Thus, canceling sound source 52 receives the canceling signal via canceling signal output terminal 12. Canceling sound source 52 emits canceling sound N1 based on the canceling signal.

Error signal source 53 detects a residual sound resulting from interference between noise N0 and canceling sound N1 emitted from canceling sound source 52 according to the canceling signal, and provides an error signal corresponding to the residual sound. Then, the error signal is inputted to error signal input terminal 13 (S14). Error signal input terminal 13 is an exemplary error signal input unit, particularly a terminal formed by metal, etc.

Next, simulated acoustic transfer characteristic filter Unit 16 generates a filtered reference signal by adjusting the reference signal using simulated transfer characteristics which simulate acoustic transfer characteristics from canceling signal output terminal 12 to error signal input terminal 13 (S15). The simulated transfer characteristics are measured in space 57 in advance, and stored on storage 18. It should be noted that the simulated transfer characteristics may be defined by an algorithm which uses no predetermined value.

Storage 18 is a storage device storing the simulated transfer characteristics. Storage 18 also stores adaptive filter coefficients described below, etc. Specifically, storage 18 is implemented as a semiconductor memory, etc. It should be noted that when signal processor 14 is implemented as a processor such as a DSP, storage 18 also stores a control program to be executed by the processor. Storage 18 also may store the other parameters to be used for signal processing performed by signal processor 14.

Filter coefficient updater 17 sequentially updates adaptive filter coefficient W based on the error signal and the generated filtered reference signal (S16).

Specifically, filter coefficient updater 17 uses a least mean square (LMS) method to calculate adaptive filter coefficient W in such a manner that the sum of squares of the error signal is minimized, and provides the calculated adaptive filter coefficient to adaptive filter unit 15. Furthermore, filter coefficient updater 17 sequentially updates the adaptive filter coefficient. Given the vector of the error signal as "e", and the vector of the filtered reference signal as "R", adaptive filter coefficient W is expressed by (Equation 1) below. It should be noted that n is a natural number and represents the n-th sample in a sampling period Ts. Here, $\beta$ is a scalar quantity and a step size parameter which determines an update amount of adaptive filter coefficient W per sampling.

[Math. 1]

$$W(n+1)=W(n)-\mu\cdot e(n)\cdot R(n) \quad \text{(Equation 1)}$$

It should be noted that filter coefficient updater 17 may update adaptive filter coefficient W using a method other than the LMS method.

[Example 1 of Abnormal Sound Suppression Operation]

In the meanwhile, the reference signal includes an intended signal component having correlation with noise N0 and reference signal noise having less correlation with noise N0. The reference signal noise includes signal noise emitted from reference signal source 51 itself, signal noise generated in a process until the reference signal provided from reference signal source 51 is inputted to reference signal input terminal 11, and the like.

When noise N0 is small and thus in the reference signal, the signal level of the intended signal component having correlation with noise N0 is lower than the signal level of the reference signal noise, canceling sound N1 is emitted from canceling sound source 52 based on the reference signal noise having less correlation with noise N0. Thus, canceling sound N1 itself results in an abnormal sound inside the cabin.

In view of this, active noise control device 10 performs an abnormal sound suppression operation for suppressing such an abnormal sound. As shown in FIG. 2, active noise control device 10 includes, as elements for the abnormal sound suppression operation, controller 20, threshold controller 21, and adjuster 22.

Controller 20 decreases the signal level of the canceling signal when the signal level of the reference signal inputted to reference signal input terminal 11 is lower than a threshold. This threshold is changed based on the signal level of the error signal by threshold controller 21. The signal level of the canceling signal is decreased by multiplying the canceling signal by the level adjustment factor $\alpha$ ($0\leq\alpha<1$) in adjuster 22.

Figure 4:
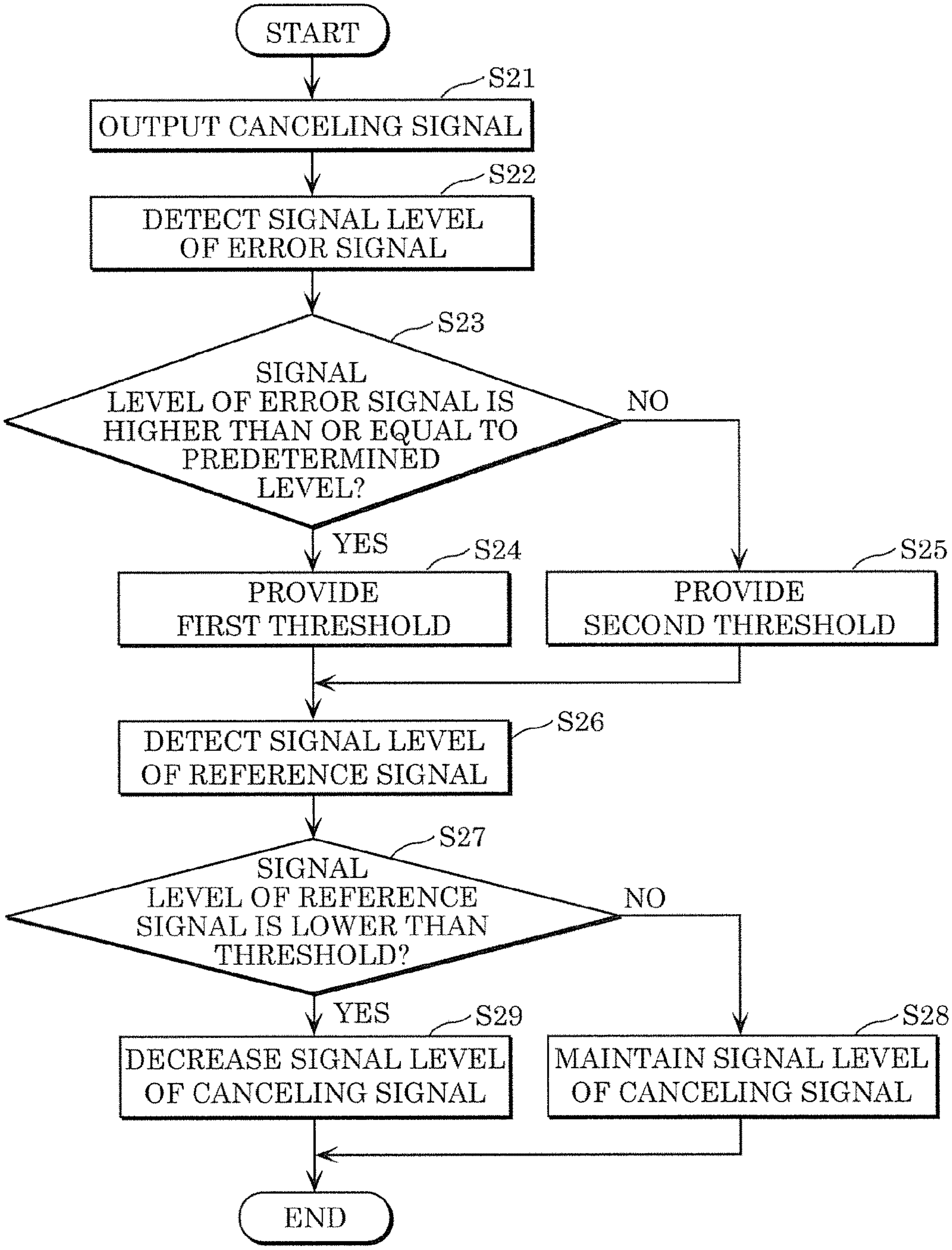
FIG. 4 is a flow chart illustrating example 1 of an abnormal sound suppression operation of the active noise control device according to embodiment 1.

Hereinafter, the abnormal sound suppression operation will be described with reference to a flowchart. FIG. 4 is the flow chart illustrating example 1 of the abnormal sound suppression operation of active noise control device 10.

When adaptive filter unit 15 outputs the canceling signal to canceling signal output terminal 12 (S21), threshold controller 21 detects the signal level of the error signal inputted to error signal input terminal 13 (S22), and determines whether or not the signal level of the error signal is higher than or equal to a predetermined level (S23). It should be noted that the signal level described here means a broad signal level. In this case, the signal level includes a maximum of the absolute value of the signal level, an average of the absolute value of the signal level, and a root mean square (RMS) of the signal level.

When the signal level of the error signal is higher than or equal to the predetermined level, the cabin is comparatively noisy. Even if canceling sound N1 is emitted based on the reference signal noise having less correlation with noise N0, members inside the cabin would be less likely to perceive canceling sound N1 as the abnormal sound. In other words, it would be less necessary that controller 20 decreases the signal level of the canceling signal. On the other hand, when the signal level of the error signal is lower than the predetermined level, the cabin is quiet, and thus canceling sound N1 would be more likely to be perceived as the abnormal sound. In other words, it would be more necessary that controller 20 decreases the signal level of the canceling signal.

In view of this, threshold controller 21 provides the first threshold to controller 20 (S24) when determining that the signal level of the error signal is higher than or equal to the predetermined level (Yes at S23), and provides the second threshold which is higher than the first threshold to controller 20 (S25) when determining that the signal level of the error signal is lower than the predetermined level (No at S23). In other words, threshold controller 21 decreases the threshold with increase in the signal level of the error signal.

With this, when the signal level of the error signal is high and noise N0 would be large, the threshold is decreased to prevent the signal level of the reference signal from frequently falling below the threshold. In other words, the control for decreasing the signal level of the canceling signal (processing at step S29 described below) is rarely activated by controller 20.

Next, controller 20 detects the signal level of the reference signal inputted to reference signal input terminal 11 (S26), and determines whether or not the detected signal level is lower than the threshold provided from threshold controller 21 (S27). Specifically, the threshold provided from threshold controller 21 is either one of the first threshold and the second threshold.

Controller 20 performs no control when determining that the signal level of the reference signal is higher than or equal to the threshold (No at S27). With this, the signal level of the canceling signal is maintained (S28).

On the other hand, the controller decreases the signal level of the canceling signal (S29) when determining the signal level of the reference signal is lower than the threshold (Yes at S27).

At step S29, controller 20 multiplies the canceling signal provided from adaptive filter unit 15 by the level adjustment factor $\alpha$ ($0 \leq \alpha < 1$) by providing a control signal to adjuster 22, for example. With this, the signal level of the canceling signal is decreased. In the decreasing, controller 20 may perform a fade-out process in which the level adjustment factor $\alpha$ reaches the target value from 1 over some time period. With this, a popping sound caused by sudden change in the signal level of the canceling signal can be prevented. This fade time period is at least 100 ms and at most 1000 ms, for example.

It should be noted that adjuster 22 may be disposed between reference signal input terminal 11 and adaptive filter unit 15 on the path of an electrical signal. In this case, controller 20 may multiply the reference signal inputted to adaptive filter unit 15 by the level adjustment factor $\alpha$ by providing the control signal to adjuster 22, to decrease the signal level of the canceling signal. Alternatively, adjuster 22 may be disposed between filter coefficient updater 17 and adaptive filter unit 15 on the path of the electrical signal. In this case, controller 20 may multiply the filter coefficient provided from filter coefficient updater 17 by the level adjustment factor $\alpha$ by providing the control signal to adjuster 22, to decrease the signal level of the canceling signal.

According to the abnormal sound suppression operation of active noise control device 10 described above, when the signal level of the reference signal is low and thus canceling sound N1 itself may be perceived as the abnormal sound, the signal level of the canceling signal is decreased. This reduces the level of canceling sound N1, thereby suppressing the abnormal sound.

Furthermore, in the abnormal sound suppression operation of active noise control device 10, the threshold is controlled according to the signal level of a noise signal. Thus, the abnormal sound suppression operation of active noise control device 10 can be more effective than the conventional abnormal sound suppression operation in which the signal level of the canceling signal is decreased based on a comparison between a static threshold and the signal level of the reference signal.

It should be noted that the exemplary operation of FIG. 4 shows an example in which the signal level of the canceling signal is decreased (hereinafter, also referred to as a signal-level decrease operation) while the canceling signal is normally provided. Here, contrary to FIG. 4, the restoring of the signal level (hereinafter, also referred to as a signal-level restoration operation) while providing the canceling signal with signal level decreased by the level adjustment factor $\alpha$ is also based on a comparison between the signal level of the reference signal and the threshold.

Specifically, when the signal level of the inputted reference signal is higher than or equal to the threshold, controller 20 provides a control signal for instructing adjuster 22 to change the level adjustment factor $\alpha=1$, thereby stopping decreasing the signal level of the canceling signal. Accordingly, the signal level of the canceling signal is restored to its original signal level.

Here, the first threshold during the signal-level restoration operation may be the same value as the first threshold during the signal-level decrease operation, but may be higher than the first threshold during the signal-level decrease operation. In other words, the first threshold may have hysteresis. With this, it can be prevented that the signal level of the canceling signal (the level adjustment factor $\alpha$) is frequently changed. Similarly, the second threshold during the signal-level restoration operation may be the same value as the second threshold during the signal-level decrease operation, but may be higher than the second threshold during the signal-level decrease operation. In other words, the second threshold may have hysteresis. With this, it can be prevented that the signal level of the canceling signal is frequently changed.

In the signal-level restoration operation, controller 20 may perform a fade-in process in which the level adjustment factor α reaches 1 over some time period. With this, a popping sound caused by sudden change in the signal level of the canceling signal can be prevented. This fade time period is at least 100 ms and at most 1000 ms, for example.

[Example 2 of Abnormal Sound Suppression Operation]

Figure 5:
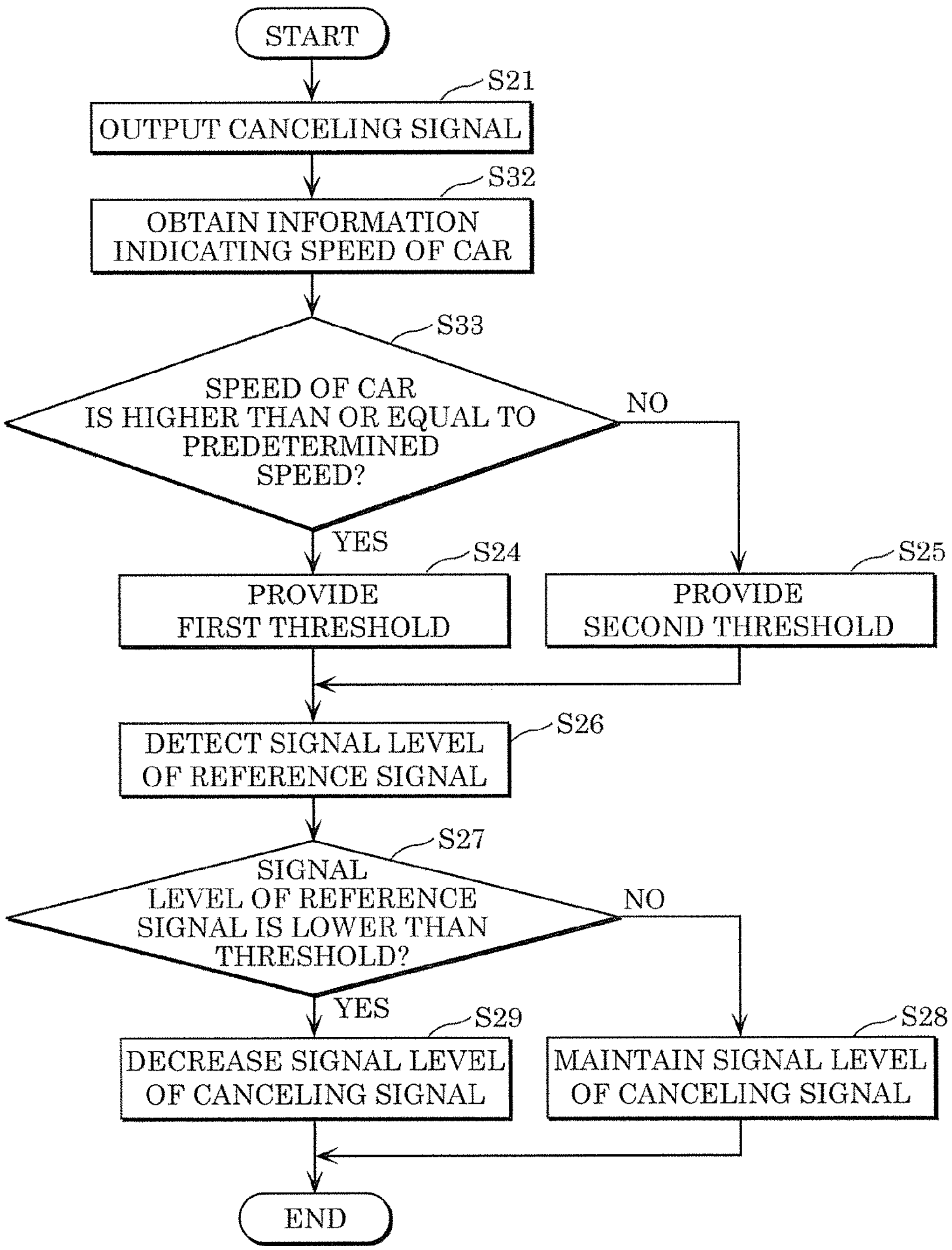
FIG. 5 is a flow chart illustrating example 2 of the abnormal sound suppression operation of the active noise control device according to embodiment 1.

Threshold controller 21 may change the threshold based on information on car 50 obtained from car controller 55 via car information input terminal 19, instead of the signal level of the error signal. Hereinafter, such example 2 of the abnormal sound suppression operation will be described with reference to a flowchart. FIG. 5 is the flow chart illustrating example 2 of the abnormal sound suppression operation of active noise control device 10. It should be noted that in the following example 2, parts different from those of example 1 will be described in detail, and the same parts are not described here.

As shown in FIG. 5, in example 2, information indicating a speed of car 50 is used as the information on car 50. When adaptive filter unit 15 outputs the canceling signal to canceling signal output terminal 12 (S21), threshold controller 21 obtains information indicating a speed of the car inputted to car information input terminal 19 (S32) from car controller 55, and determines whether or not the speed of car 50 is higher than or equal to a predetermined speed (S33).

When the speed of car 50 is higher than or equal to the predetermined speed, the cabin is comparatively noisy. Canceling sound N1 would be less likely to be perceived as the abnormal sound. In other words, it would be less necessary that controller 20 decreases the signal level of the canceling signal. On the other hand, when the speed of car 50 is lower than the predetermined speed, the cabin is quiet, and thus canceling sound N1 would be more likely to be perceived as the abnormal sound. In other words, it would be more necessary that controller 20 decreases the signal level of the canceling signal.

In view of this, threshold controller 21 provides the first threshold to controller 20 (S24) when determining that the speed of car 50 is higher than or equal to the predetermined speed (Yes at S33), and provides the second threshold which is higher than the first threshold to controller 20 (S25) when determining that the speed of car 50 is lower than the predetermined speed (No at S33). In other words, threshold controller 21 decreases the threshold with increase in the speed of car 50. With this, when the speed of the car is high and noise N0 would be large, the threshold is decreased to prevent the signal level of the reference signal from frequently falling below the threshold. In other words, the control for decreasing the signal level of the canceling signal is rarely activated by controller 20. It should be noted that steps following step S26 are the same as those of example 1.

In the above example 2, the threshold is controlled according to the speed of car 50. Thus, the same effect as example 1 can be achieved by the abnormal sound suppression operation of active noise control device 10. In other words, example 2 is more effective than the conventional abnormal sound suppression operation in which the signal level of the canceling signal is decreased based on a comparison between a static threshold and the signal level of the reference signal.

It should be noted that the information indicating the speed of car 50 is an example of information indicating a driving state of car 50. Threshold controller 21 may change the threshold based on other information indicating the driving state of car 50. For example, threshold controller 21 may change the threshold based on information indicating a state of an engine of car 50.

For example, when car 50 is a hybrid electric vehicle (HEV) or an electric vehicle (EV), the cabin is quiet if car 50 is moved by the motor while stopping the engine. Thus, canceling sound N1 would be more likely to be perceived as the abnormal sound. In other words, it would be more necessary that controller 20 decreases the signal level of the canceling signal. On the other hand, when car 50 is moved by the engine, the cabin is comparatively noisy. Canceling sound N1 would be less likely to be perceived as the abnormal sound. In other words, it would be less necessary that controller 20 decreases the signal level of the canceling signal.

In view of this, threshold controller 21 decreases the threshold during rotation of the engine to less than a threshold during non-rotation of the engine. With this, when the engine is rotating and noise N0 would be large, the threshold is decreased to prevent the signal level of the reference signal from frequently falling below the threshold. In other words, the control for decreasing the signal level of the canceling signal is rarely activated by controller 20.

Furthermore, the information on car 50 is not limited to the information indicating the driving state of car 50, and may be information indicating a state of equipment in car 50. For example, the information indicating the state of the equipment in car 50 is information indicating a state of an air conditioner in car 50.

In this case, when a fan speed of the air conditioner is larger than or equal to a predetermined amount, the cabin is comparatively noisy. Canceling sound N1 would be less likely to be perceived as the abnormal sound. In other words, it would be less necessary that controller 20 decreases the signal level of the canceling signal. On the other hand, when the fan speed of the air conditioner is smaller than the predetermined amount, the cabin is quiet. Canceling sound N1 would be more likely to be perceived as the abnormal sound. In other words, it would be more necessary that controller 20 decreases the signal level of the canceling signal.

In view of this, threshold controller 21 decreases the threshold with increase in the fan speed of the air conditioner. With this, when the fan speed of the air conditioner is large and noise N0 would be large, the threshold is decreased to prevent the signal level of the reference signal from frequently falling below the threshold. In other words, the control for decreasing the signal level of the canceling signal is rarely activated by controller 20.

(Variations)

When the signal level of the inputted reference signal is lower than a threshold, controller 20 can decrease the signal level of the canceling signal to stop the emission of canceling sound N1. Specifically, controller 20 can stop the emission of canceling sound N1 by providing a control signal for instructing adjuster 22 to change the level adjustment factor α=0. In this case, if the filter coefficient continues to be updated by filter coefficient updater 17 while forcing canceling sound N1 to stop through controller 20, the coefficient becomes too large when the signal level of the canceling sound is restored to its original signal level. Accordingly, large canceling sound N1 is emitted when the signal level of canceling signal is restored. This causes the abnormal sound.

In view of this, during the stop of canceling sound N1, controller 20 may cause filter coefficient updater 17 to stop updating of the coefficient of the adaptive filter. With this, active noise control device 10 can prevent large canceling sound N1 from being emitted when the signal level of the canceling sound is restored to its original signal level.

It should be noted that storage 18 preferably stores a filter coefficient immediately before the stop of canceling sound N1, which is used when the signal level of the canceling sound is restored to its original signal level.

Embodiment 2

Example 1 of Embodiment 2

Figure 6:
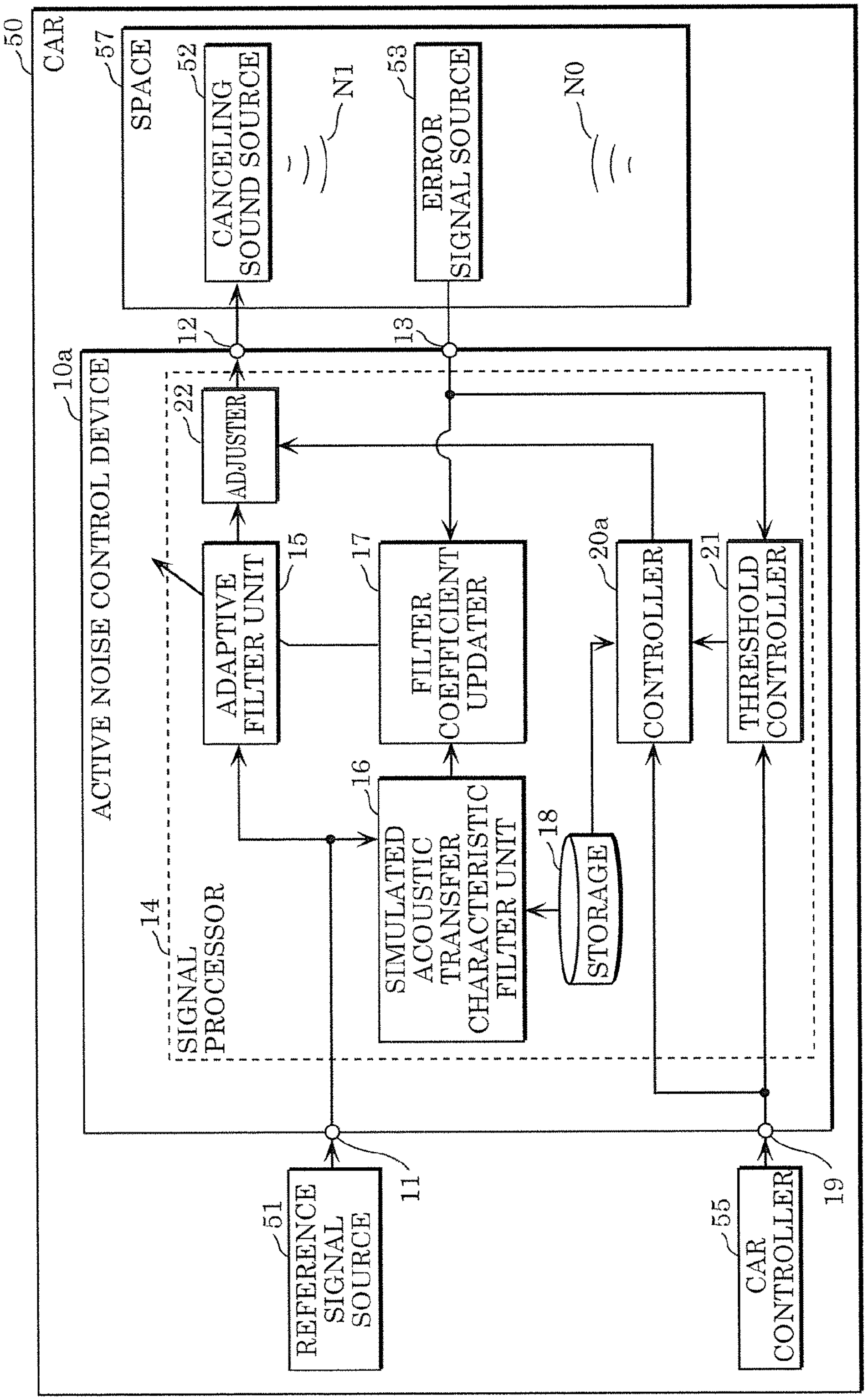
FIG. 6 is a block diagram illustrating the functional configuration of an active noise control device according to embodiment 2.

Controller 20*a* may decrease the signal level of the canceling signal based on the information on car 50 instead of the signal level of the reference signal. Hereinafter, such embodiment 2 will be described. FIG. 6 is a block diagram illustrating the functional configuration of an active noise control device according to embodiment 2.

Figure 7:
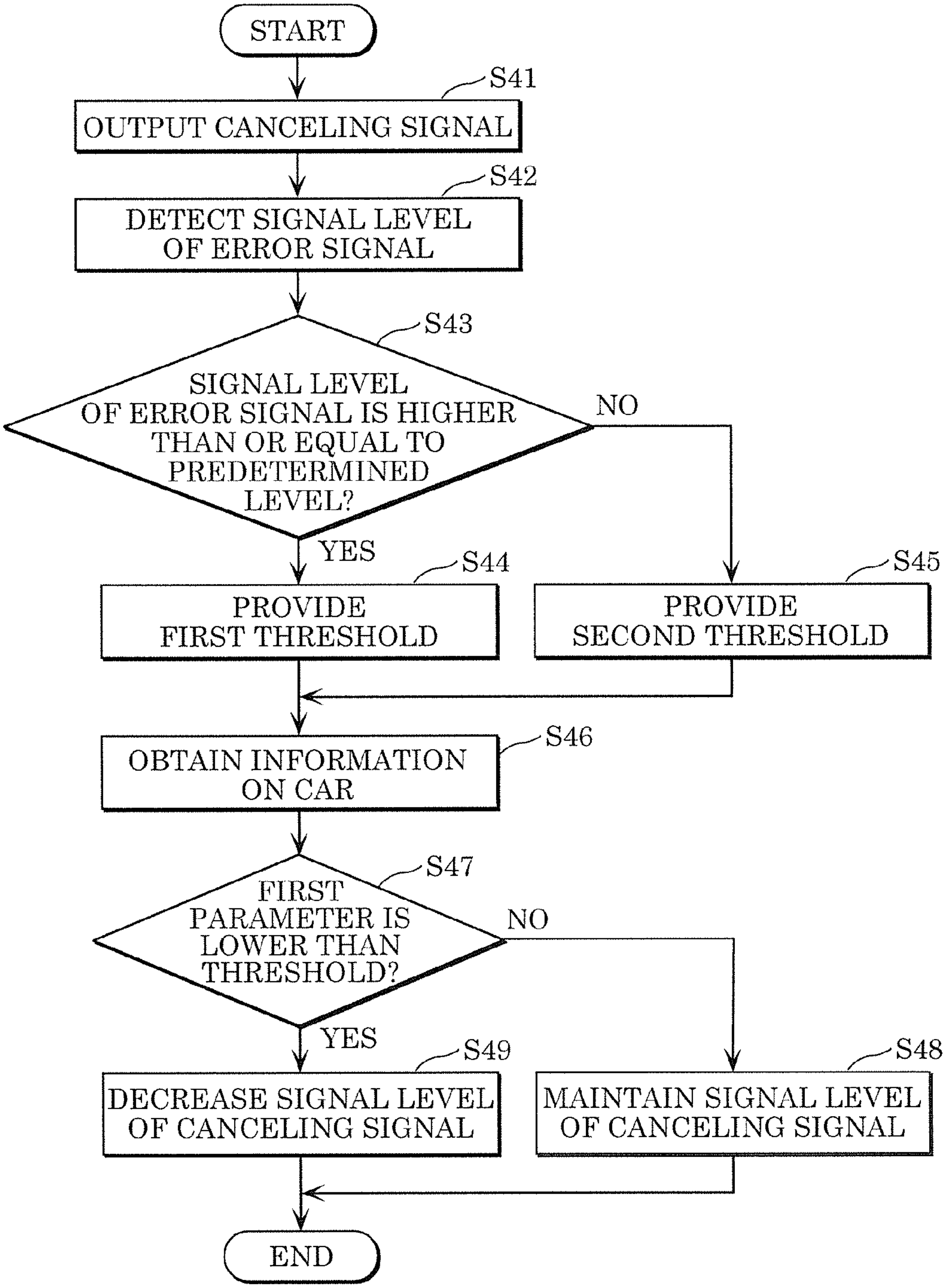
FIG. 7 is a flow chart illustrating example 1 of an abnormal sound suppression operation of the active noise control device according to embodiment 2.

As shown in FIG. 6, active noise control device 10*a* according to embodiment 2 includes controller 20*a* that obtains the information on car 50 instead of the reference signal. FIG. 7 is a flow chart illustrating example 1 of an abnormal sound suppression operation of active noise control device 10*a*.

When adaptive filter unit 15 outputs the canceling signal to canceling signal output terminal 12 (S41), threshold controller 21 detects the signal level of the error signal inputted to error signal input terminal 13 (S42), and determines whether or not the signal level of the error signal is higher than or equal to a predetermined level (S43).

When the signal level of the error signal is larger than or equal to the predetermined level, the cabin is comparatively noisy. Canceling sound N1 would be less likely to be perceived as the abnormal sound. In other words, it would be less necessary that controller 20*a* decreases the signal level of the canceling signal. On the other hand, when the signal level of the error signal is less than the predetermined level, the cabin is quiet. Canceling sound N1 would be more likely to be perceived as the abnormal sound. In other words, it would be more necessary that the signal level of the canceling signal is decreased.

In view of this, threshold controller 21 provides the first threshold to controller 20*a* (S44) when determining that the signal level of the error signal is higher than or equal to the predetermined level (Yes at S43), and provides the second threshold which is higher than the first threshold to controller 20*a* (S45) when determining that the signal level of the error signal is lower than the predetermined level (No at S43). In other words, threshold controller 21 decreases the threshold with increase in the signal level of the error signal.

With this, when the signal level of the error signal is high and noise N0 would be large, the threshold is decreased to prevent the first parameter from frequently falling below the threshold. In other words, the control for decreasing the signal level of the canceling signal (processing at step S49 described below) is rarely activated by controller 20*a*.

Next, controller 20*a* obtains the information on car 50 inputted to car information input terminal 19 (S46), and determines whether or not the first parameter included in the information on car 50 is lower than the threshold provided from threshold controller 21 (S47). Specifically, the threshold provided from threshold controller 21 is either one of the first threshold and the second threshold. For example, the first parameter is a parameter indicating a speed of car 50, and the first parameter higher than or equal to the threshold corresponds to the speed of car 50 higher than or equal to the threshold.

When the speed of car 50 is higher than or equal to the threshold, the cabin is comparatively noisy. Canceling sound N1 itself would be less likely to be perceived as the abnormal sound. In view of this, controller 20*a* performs no control when determining that the first parameter is higher than or equal to the threshold (No at S47). With this, the signal level of the canceling signal is maintained (S48).

On the other hand, when the speed of car 50 is less than the threshold, the cabin is quiet. Canceling sound N1 would be likely to be perceived as the abnormal sound. In view of this, the controller decreases the signal level of the canceling signal (S49) when determining the signal level of the first parameter is lower than the threshold (Yes at S47). Specific example of the control for decreasing the signal level of the canceling signal is the same as that of embodiment 1.

According to the abnormal sound suppression operation of active noise control device 10*a* described above, when the first parameter indicating the speed of car 50 is lower than the threshold and thus canceling sound N1 itself may be perceived as the abnormal sound, the signal level of the canceling signal is decreased. This reduces the level of canceling sound N1, thereby suppressing the abnormal sound. Furthermore, the determination based on the information on car 50 at step S47 is advantageous in that it is easier than the determination based on the signal level of the reference signal at step S27 in embodiment 1.

Furthermore, in the abnormal sound suppression operation of active noise control device 10*a,* the threshold is controlled according to the signal level of a noise signal. Thus, the abnormal sound suppression operation of active noise control device 10*a* can be more effective than the conventional abnormal sound suppression operation in which the signal level of the canceling signal is decreased based on a comparison between a static threshold and the signal level of the reference signal.

It should be noted that example 1 in FIG. 7 shows the signal-level decrease operation, but the signal-level restoration operation of active noise control device 10*a* is also performed based on a comparison between the first parameter and the threshold.

Specifically, when the signal level of the first parameter is higher than or equal to the threshold, controller 20*a* provides a control signal for instructing adjuster 22 to change the level adjustment factor thereby stopping decreasing the signal level of the canceling signal. Accordingly, the signal level of the canceling signal is restored to its original signal level. The signal-level restoration operation of active noise control device 10*a* is the same as the signal-level restoration operation described in embodiment 1, except performed based on a comparison between the first parameter and the threshold.

Example 2 of Embodiment 2

Figure 8:
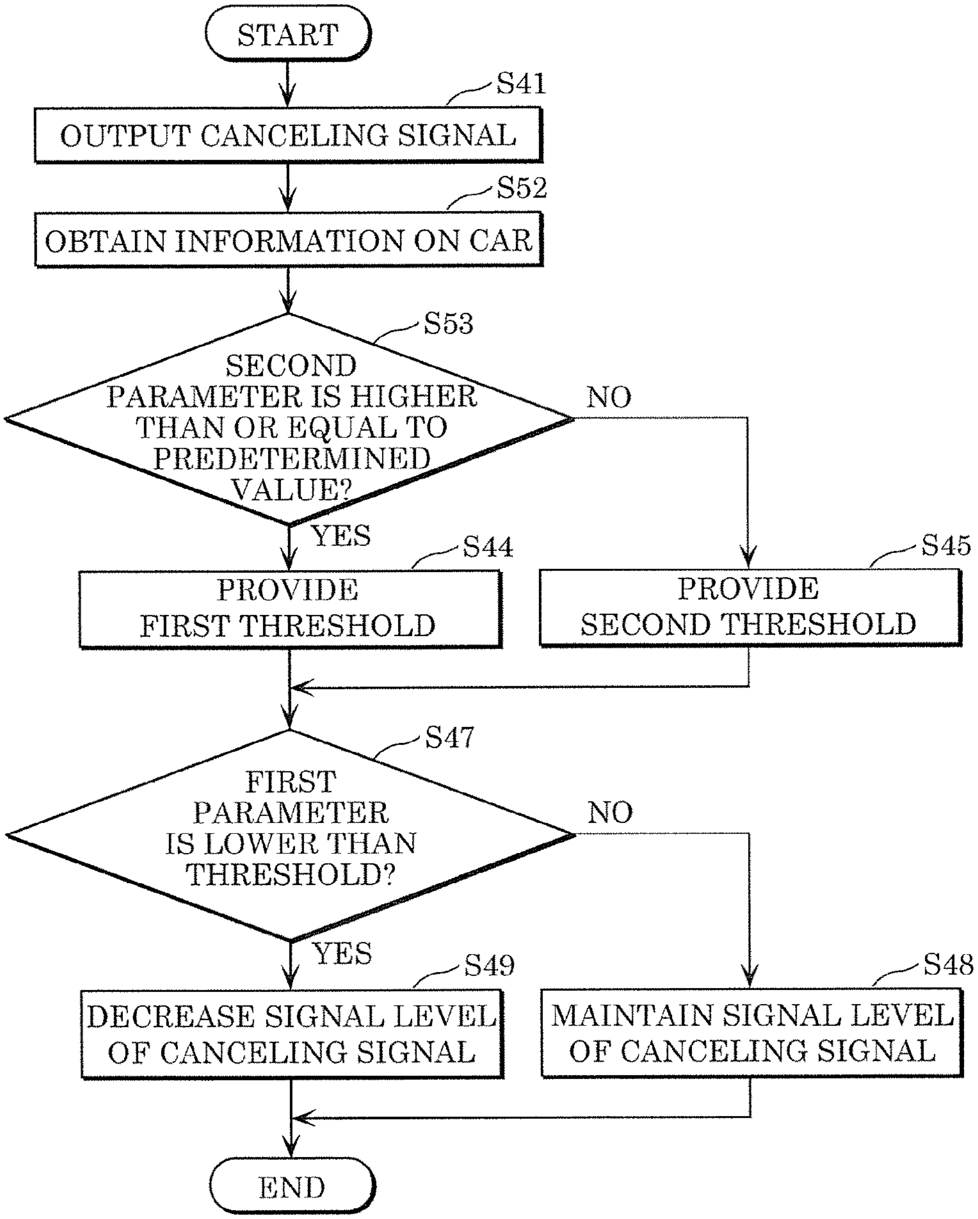
FIG. 8 is a flow chart illustrating example 2 of the abnormal sound suppression operation of the active noise control device according to embodiment 2.

Threshold controller 21 may change the threshold based on the information on car 50 obtained from car controller 55 via car information input terminal 19, instead of the signal level of the error signal. Hereinafter, such example 2 of the abnormal sound suppression operation will be described with reference to a flowchart. FIG. 8 is a flow chart illustrating example 2 of the abnormal sound suppression operation of active noise control device 10*a*. It should be noted that in the following example 2, parts different from those of example 1 of embodiment 2 will be described in detail, and the same parts are not described here.

As shown in FIG. 8, in example 2 of embodiment 2, when adaptive filter unit 15 outputs the canceling signal to canceling signal output terminal 12 (S41), threshold controller 21 obtains information on car 50 inputted to car information input terminal 19, from car controller 55 (S52). The information on car 50 includes the first parameter and the second parameter. For example, the first parameter is a parameter indicating a speed of car 50, and the second parameter is a parameter indicating a state of an engine of car 50. For example, the second parameter is a parameter indicating a rotation speed of the engine of car 50. The second parameter is different from the first parameter.

Threshold controller 21 determines whether or not the second parameter is higher than or equal to a predetermined value (S53). In other words, threshold controller 21 determines whether or not the rotation speed of the engine of car 50 is higher than or equal to the predetermined value.

For example, when car 50 is a HEV or an EV, the cabin is quiet if car 50 is moved by the motor while stopping the engine. Thus, canceling sound N1 would be more likely to be perceived as the abnormal sound. In other words, it would be more necessary that controller 20*a* decreases the signal level of the canceling signal. On the other hand, when car 50 is moved by the engine, the cabin is comparatively noisy. Canceling sound N1 would be less likely to be perceived as the abnormal sound. In other words, it would be less necessary that controller 20*a* decreases the signal level of the canceling signal.

In view of this, threshold controller 21 provides the first threshold to controller 20*a* (S44) when determining that the rotation speed of the engine of car 50 is higher than or equal to the predetermined value (Yes at S53), and provides the second threshold which is higher than the first threshold to controller 20*a* (S45) when determining that the rotation speed of the engine of car 50 is lower than the predetermined value (No at S53). In other words, threshold controller 21 decreases the threshold with increase in the rotation speed of the engine. Steps following this step are the same as those of example 1 of embodiment 2, except omitted step S46.

With this, when the rotation speed of the engine is high and noise N0 would be large, the threshold is decreased to prevent the first parameter from frequently falling below the threshold. In other words, the control for decreasing the signal level of the canceling signal is rarely activated by controller 20*a*.

It should be noted that the second parameter is not limited to the parameter indicating the state of car 50 such as the parameter indicating the state of the engine of car 50. The second parameter may be a parameter indicating the state of the equipment in car 50. Specifically, the second parameter may be a parameter indicating the state of the air conditioner in car 50. More specifically, the second parameter may be a parameter indicating the fan speed of the air conditioner in car 50.

In this case, when the fan speed of the air conditioner is larger than or equal to a predetermined amount, the cabin is comparatively noisy. Canceling sound N1 would be less likely to be perceived as the abnormal sound. In other words, it would be less necessary that controller 20*a* decreases the signal level of the canceling signal. On the other hand, when the fan speed of the air conditioner is smaller than the predetermined amount, the cabin is quiet. Canceling sound N1 would be more likely to be perceived as the abnormal sound. In other words, it would be more necessary that controller 20*a* decreases the signal level of the canceling signal.

In view of this, threshold controller 21 decreases the threshold with increase in the fan speed of the air conditioner. With this, when the fan speed of the air conditioner is large and noise N0 would be large, the threshold is decreased to prevent the first parameter from frequently falling below the threshold. In other words, the control for decreasing the signal level of the canceling signal is rarely activated by controller 20*a*.

Variations of Embodiment 2

When the first parameter included in the information on car 50 is lower than the threshold, controller 20*a* can decrease the signal level of the canceling signal to stop the emission of canceling sound N1. Specifically, controller 20*a* can stop the emission of canceling sound N1 by providing a control signal for instructing adjuster 22 to change the level adjustment factor $\alpha=0$. In this case, if the filter coefficient continues to be updated by filter coefficient updater 17 while forcing canceling sound N1 to stop through controller 20*a*, the coefficient becomes too large when the signal level of canceling sound is restored to its original signal level. Accordingly, large canceling sound N1 is emitted when the signal level of canceling signal is restored. This causes the abnormal sound.

In view of this, during the stop of canceling sound N1, controller 20*a* may cause filter coefficient updates 17 to stop updating of the coefficient of the adaptive filter. With this, active noise control device 10*a* can prevent large canceling sound N1 from being emitted when the signal level of the canceling sound is restored to its original signal level.

It should be noted that storage 18 preferably stores a filter coefficient immediately before the stop of canceling sound N1, which is used when the signal level of the canceling sound is restored to its original signal level.

Embodiment 3

Active noise control device 10 described in embodiment 1 may make the determination based on the information on car 50 as well as the determination based on the signal level of the reference signal to determine whether or not the signal level of the canceling signal is decreased. In other words, further when the first parameter included in the information on car 50 is lower than the threshold, controller 20 may decrease the signal level of the canceling signal. Specifically, further when the speed of car 50 indicated by the first parameter is lower than the threshold, controller 20 may decrease the signal level of the canceling signal.

Similarly, active noise control device 10*a* described in embodiment 2 may make the determination based on the signal level of the reference signal as well as the determination based on the information on car 50 to determine whether or not the signal level of the canceling signal is decreased. In other words, further when the signal level of the inputted reference signal is lower than the threshold, controller 20*a* may decrease the signal level of the canceling signal.

Figure 9:
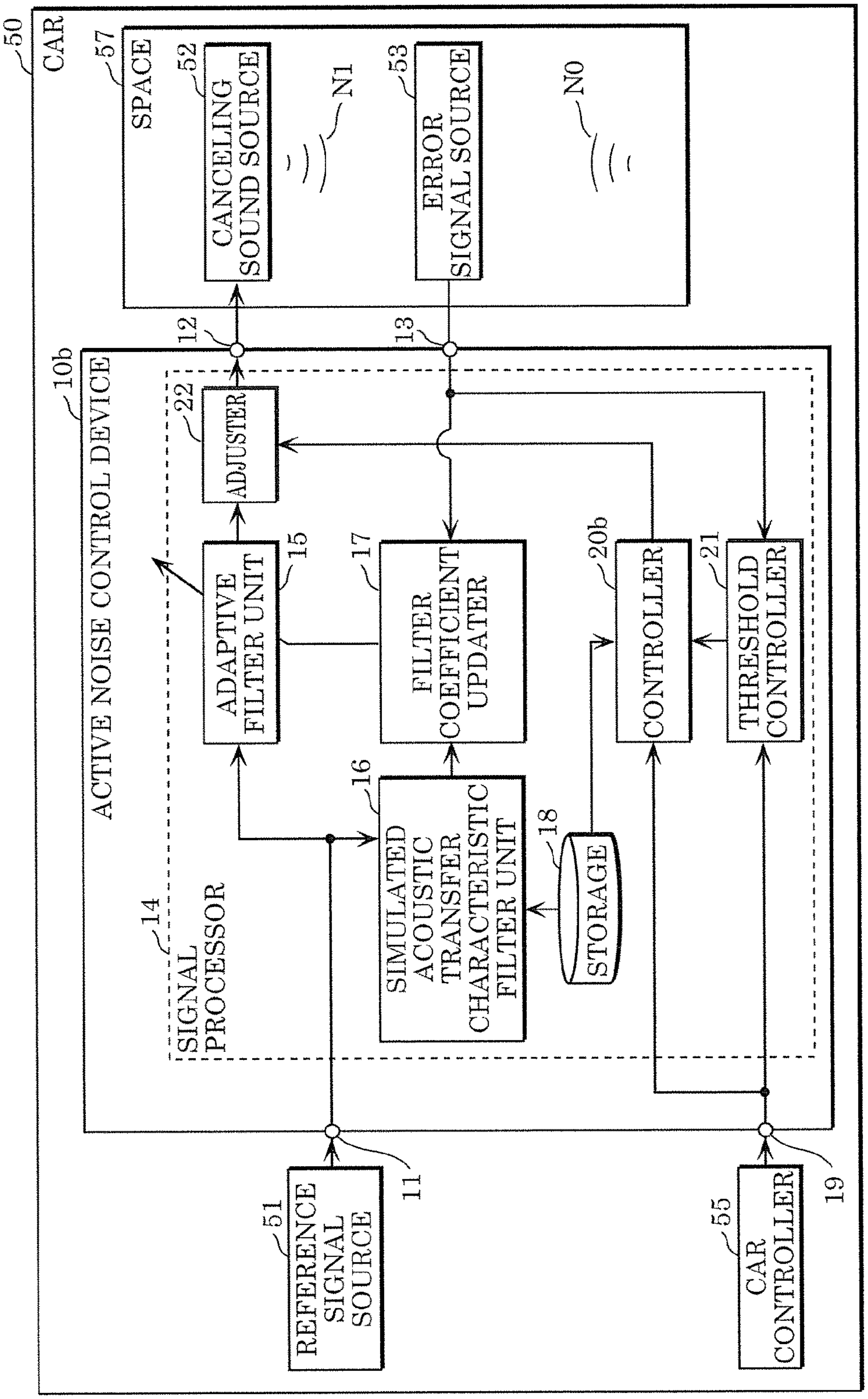
FIG. 9 is a block diagram illustrating the functional configuration of an active noise control device according to embodiment 3.

FIG. 9 is a block diagram illustrating the functional configuration of an active noise control device according to embodiment 3, which can make such two determinations. In active noise control device 10*b* as shown in FIG. 9, controller 20*b* can obtain both the reference signal and the information on the car via reference signal input terminal 11 and car information input terminal 19, respectively.

Thus, active noise control device 10*b* can make two determinations: the determination based on the signal level of the reference signal; and the determination based on the information on car 50, to determine whether or not the signal level of the canceling signal is decreased. For the two determinations, the signal level of canceling signal may be decreased when the requirement for at least one of the two determinations is satisfied, or when both requirements for the two determinations are satisfied.

Furthermore, in this case, for each or either one of the two determinations, the threshold to be used for the determination may be changed by threshold controller 21. Any method described above may be used to change the threshold.

Advantageous Effects, etc.

As described above, active noise control device 10 is an active noise control device that reduces noise N0 inside a cabin of car 50. Active noise control device 10 includes: reference signal input terminal 11 that receives a reference signal having correlation with the noise; adaptive filter unit 15 that generates a canceling signal by applying an adaptive filter to the reference signal received; canceling signal output terminal 12 that receives the canceling signal generated; error signal input terminal 13 that receives an error signal corresponding to a residual sound resulting from interference between noise N0 and canceling sound N1 emitted from canceling sound source 52 according to the canceling signal; simulated acoustic transfer characteristic filter unit 16 that generates a filtered reference signal by adjusting the reference signal using simulated transfer characteristics which simulate acoustic transfer characteristics from canceling signal output terminal 12 to error signal input terminal 13; filter coefficient updater 17 that sequentially updates a coefficient of the adaptive filter using the error signal and the filtered reference signal generated; controller 20 that decreases a signal level of the canceling signal when a signal level of the reference signal received is lower than a threshold; and threshold controller 21 that changes the threshold based on at least one of a signal level of the error signal and information on car 50. Reference signal input terminal 11 is an example of the reference signal input unit. Canceling signal output terminal 12 is an example of the canceling signal output unit. Error signal input terminal 13 is an example of the error signal input unit.

With this, when the signal level of the reference signal is lower than the threshold and thus canceling sound N1 itself may be perceived as the abnormal sound, the signal level of the canceling signal is decreased. This reduces the level of canceling sound N1, thereby suppressing the abnormal sound.

Furthermore, in active noise control device 10, the threshold is controlled based on at least one of the signal level of the error signal and the information on car 50, and thus the abnormal sound suppression operation of active noise control device 10 can be more effective than the conventional abnormal sound suppression operation in which the signal level of the canceling signal is decreased based on a comparison between a static threshold and the signal level of the reference signal.

Furthermore, for example, threshold controller 21 decreases the threshold with increase in the signal level of the error signal.

With this, when the signal level of the error signal is high and noise N0 would be large, the threshold is decreased to prevent the signal level of the reference signal from frequently falling below the threshold. In other words, the control for decreasing the signal level of the canceling signal is rarely activated by controller 20. Therefore, active noise control device 10 can appropriately emit canceling sound N1.

Furthermore, for example, the information on car 50 is information indicating a driving state of car 50.

With this, threshold controller 21 can change the threshold based on the information indicating the driving state of car 50.

Furthermore, for example, the information indicating the driving state of car 50 is information indicating a speed of car 50, and threshold controller 21 decreases the threshold with increase in the speed of car 50.

With this, when the speed of the car is high and noise N0 would be large, the threshold is decreased to prevent the signal level of the reference signal from frequently falling below the threshold. In other words, the control for decreasing the signal level of the canceling signal is rarely activated by controller 20. Therefore, active noise control device 10 can appropriately emit canceling sound N1.

Furthermore, for example, the information indicating the driving state of car 50 is information indicating a state of an engine of car 50, and threshold controller 21 decreases the threshold during rotation of the engine to less than a threshold during non-rotation of the engine.

With this, when the engine is rotating and noise N0 would be large, the threshold is decreased to prevent the signal level of the reference signal from frequently falling below the threshold. In other words, the control for decreasing the signal level of the canceling signal is rarely activated by controller 20. Therefore, active noise control device 10 can appropriately emit canceling sound N1.

Furthermore, for example, the information on car 50 is information indicating a state of equipment in car 50.

With this, threshold controller 21 can change the threshold based on the information indicating the state of the equipment in car 50.

Furthermore, for example, the information indicating the state of the equipment in car 50 is information indicating a state of an air conditioner in car 50, and threshold controller 21 decreases the threshold with increase in a fan speed of the air conditioner.

With this, when the fan speed of the air conditioner is large and noise N0 would be large, the threshold is decreased to prevent the signal level of the reference signal from frequently falling below the threshold. In other words, the control for decreasing the signal level of the canceling signal is rarely activated by controller 20. Therefore, active noise control device 10 can appropriately emit canceling sound N1.

Furthermore, for example, when the signal level of the reference signal received is lower than the threshold, controller 20 decreases the signal level of the canceling signal to stop emission of canceling sound N1, and causes filter coefficient updater 17 to stop updating of the coefficient of the adaptive filter.

With this, active noise control device 10 can prevent large canceling sound N1 from being emitted when the signal level of the canceling sound is restored to its original signal level.

Furthermore, for example, like controller 20*b,* controller 20 further performs control to decrease the signal level of the canceling signal when a first parameter included in the information on car 50 is lower than a threshold.

With this, when at least one of the requirement that the signal level of the received reference signal is lower than the threshold and the requirement that the first parameter included in the information on car 50 is lower than the threshold is satisfied, the signal level of the canceling signal is decreased. In other words, the control for decreasing the signal level of the canceling signal is more reliably performed.

Furthermore, active noise control device 10*a* is an active noise control device that reduces noise N0 inside a cabin of car 50. Active noise control device 10*a* includes: reference signal input terminal 11 that receives a reference signal having correlation with noise N0; adaptive filter unit 15 that generates a canceling signal by applying an adaptive filter to the reference signal received; canceling signal output terminal 12 that receives the canceling signal generated; error signal input terminal 13 that receives an error signal corresponding to a residual sound resulting from interference between noise N0 and canceling sound N1 emitted from canceling sound source 52 according to the canceling signal; simulated acoustic transfer characteristic filter unit 16 that generates a filtered reference signal by adjusting the reference signal using simulated transfer characteristics which simulate acoustic transfer characteristics from canceling signal output terminal 12 to error signal input terminal 13; filter coefficient updater 17 that sequentially updates a coefficient of the adaptive filter using the error signal and the filtered reference signal generated; car information input terminal 19 that receives information on car 50; controller 20*a* that decreases a signal level of the canceling signal when a first parameter included in the information on car 50 is lower than a threshold; and threshold controller 21 that changes the threshold based on at least one of a signal level of the error signal and a second parameter included in the information on car 50, the second parameter being different from the first parameter. Reference signal input terminal 11 is an example of the reference signal input unit. Canceling signal output terminal 12 is an example of the canceling signal output unit. Error signal input terminal 13 is an example of the error signal input unit.

With this, when the first parameter is lower than the threshold and thus canceling sound N1 itself may be perceived as the abnormal sound, the signal level of the canceling signal is decreased. This reduces the level of canceling sound N1, thereby suppressing the abnormal sound.

Furthermore, in active noise control device 10*a*, the threshold is controlled based on at least one of the signal level of the error signal and the second parameter different from the first parameter included in the information on car 50, and thus the abnormal sound suppression operation of active noise control device 10*a* can be more effective than the conventional abnormal sound suppression operation in which the signal level of the canceling signal is decreased based on a comparison between a static threshold and the signal level of the reference signal.

Furthermore, for example, threshold controller 21 decreases the threshold with increase in the signal level of the error signal.

With this, when the signal level of the error signal is high and noise N0 would be large, the threshold is decreased to prevent the first parameter from frequently falling below the threshold. In other words, the control for decreasing the signal level of the canceling signal is rarely activated by controller 20*a*. Therefore, active noise control device 10*a* can appropriately emit canceling sound N1.

Furthermore, for example, the first parameter indicates a speed of car 50, and the second parameter indicates a state of an engine of car 50. Controller 20*a* decreases the signal level of the canceling signal when the speed of car 50 is lower than the threshold, and threshold controller 21 decreases the threshold with increase in a rotation speed of the engine.

With this, when the rotation speed of the engine is high and noise N0 would be large, the threshold is decreased to prevent the first parameter from frequently falling below the threshold. In other words, the control for decreasing the signal level of the canceling signal is rarely activated by controller 20*a*. Therefore, active noise control device 10*a* can appropriately emit canceling sound N1.

Furthermore, for example, the first parameter indicates a speed of car 50, and the second parameter indicates a state of an air conditioner in car 50. Controller 20*a* decreases the signal level of the canceling signal when the speed of car 50 is lower than the threshold. Threshold controller 21 decreases the threshold with increase in a fan speed of the air conditioner.

With this, when the fan speed of the air conditioner is large and noise N0 would be large, the threshold is decreased to prevent the first parameter from frequently falling below the threshold. In other words, the control for decreasing the signal level of the canceling signal is rarely activated by controller 20*a*. Therefore, active noise control device 10*a* can appropriately emit canceling sound N1.

Furthermore, for example, like controller 20*b*, when the first parameter is lower than the threshold, controller 20*a* decreases the signal level of the canceling signal to stop emission of canceling sound N1, and causes filter coefficient updates 17 to stop updating of the coefficient of the adaptive filter.

With this, active noise control device 10*a* can prevent large canceling sound N1 from being emitted when the signal level of the canceling sound is restored to its original signal level.

Furthermore, for example, controller 20*a* further performs control to decrease the signal level of the canceling signal when a signal level of the reference signal received is lower than a threshold.

With this, when at least one of the requirement that the first parameter included in the information on car 50 is lower than the threshold and the requirement that the signal level of the received reference signal is lower than the threshold is satisfied, the signal level of the canceling signal is decreased. In other words, the control for decreasing the signal level of the canceling signal is more reliably performed.

Furthermore, car 50 includes active noise control device 10 and canceling sound source 52. Car 50 may include active noise control device 10*a* or active noise control device 10*b* instead of active noise control device 10.

Such car 50 achieves the same effect as active noise control device 10, etc.

Furthermore, an active noise control method executed by active noise control device 10, etc. is an active noise control method for reducing noise inside a cabin of car 50. The active noise control method includes: generating a canceling signal by applying an adaptive filter to a reference signal having correlation with noise N0; generating a filtered reference signal by adjusting the reference signal using simulated transfer characteristics which simulate acoustic transfer characteristics from canceling signal output terminal 12 to error signal input terminal 13, the canceling signal output terminal receiving the canceling signal, the error signal input terminal receiving an error signal corresponding to a residual sound resulting from interference between noise N0 and canceling sound N1 emitted from canceling sound source 52 according to the canceling signal generated; sequentially updating a coefficient of the adaptive filter using the error signal and the filtered reference signal generated; decreasing a signal level of the canceling signal when a signal level of the reference signal received is lower than a threshold; and changing the threshold based on at least one of a signal level of the error signal and information on car 50. Canceling signal output terminal 12 is an example of the canceling signal output unit. Error signal input terminal 13 is an example of the error signal input unit.

Such an active noise control method achieves the same effect as active noise control device 10.

Furthermore, an active noise control method executed by active noise control device 10*a*, etc. is an active noise control method for reducing noise N0 inside a cabin of car 50. The active noise control method includes: generating a canceling signal by applying an adaptive filter to a reference signal having correlation with noise N0; generating a filtered reference signal by adjusting the reference signal using simulated transfer characteristics which simulate acoustic transfer characteristics from canceling signal output terminal 12 to error signal input terminal 13, the canceling signal output terminal receiving the canceling signal, the error signal input terminal receiving an error signal corresponding to a residual sound resulting from interference between noise N0 and canceling sound N1 emitted from a canceling sound source according to the canceling signal generated; sequentially updating a coefficient of the adaptive filter using the error signal and the filtered reference signal generated; decreasing a signal level of the canceling signal when a first parameter included in information on car 50 is lower than a threshold; and changing the threshold based on at least one of a signal level of the error signal and a second parameter included in the information on car 50, the second parameter being different from the first parameter.

Such an active noise control method achieves the same effect as active noise control device 10*a*.

Other Embodiments

The foregoing has described embodiments 1 to 3, but the present disclosure is not limited to the above embodiments 1 to 3.

For example, although the threshold controller according to the above embodiment provides either one of the first threshold and the second threshold, the threshold controller may selectively provide three or more different thresholds. In other words, the threshold may be changed in three or more divided stages. Furthermore, the threshold may be defined as a function of the signal level of the error signal. This function may be a linear function or a logarithm function.

Furthermore, the configuration of the active noise control device according to each of embodiments 1 to 3 is an example. For example, the active noise control device may include a component such as a D/A converter, a filter, a power amplifier, or an A/D converter.

Furthermore, the processes performed by the active noise control device according to each of embodiments 1 to 3 are an example. For example, a part of the processes described in the foregoing embodiment may be realized by analog signal processing instead of digital signal processing.

Furthermore, for example, in embodiments 1 to 3, a process performed by a certain processing unit may be performed by a different processing unit. Furthermore, the order of multiple processes may be changed or the multiple processes may be performed in parallel.

Furthermore, in embodiments 1 to 3, each component may be realized by the configuration of dedicated hardware or by executing a software program suitable for each component. Each component may be realized by the readout and execution of a software program recorded in a recording medium such as a hard disk or a semiconductor memory by a program executer such as a CPU or a processor.

Furthermore, each component may be a circuit (or an integrated circuit). The circuits may constitute a single circuit as a whole, or may be individual circuits. Furthermore, each of the circuits may be a general-purpose circuit, or may be a dedicated circuit.

Furthermore, an overall or specific aspect of the present disclosure may be realized by a system, a device, a method, an integrated circuit, a computer program, or a computer-readable non-transitory recording medium such as a CD-ROM. Furthermore, an overall or specific aspect of the present disclosure may also be realized by any combination of a system, a device, a method, an integrated circuit, a computer program, or a computer-readable non-transitory recording medium. For example, the present disclosure may also be realized as an active noise control method, or may also be realized as a program for causing a computer or a DSP to execute the active noise control method described above. Furthermore, the present disclosure may be realized as a car or an active noise control system including the active noise control device according to the foregoing embodiments, a reference signal source, a canceling sound source, and an error signal source.

The present disclosure includes, for example, forms that can be obtained by various modifications to the respective embodiments and variations that may be conceived by those skilled in the art, and forms obtained by arbitrarily combining elements and functions in the respective embodiments without departing from the essence of the present disclosure.

INDUSTRIAL APPLICABILITY

The active noise control device according to the present disclosure is useful as an active noise control device in which the canceling sound itself is prevented from being perceived as an abnormal sound.

While various embodiments have been described herein above, it is to be appreciated that various changes in form and detail may be made without departing from the spirit and scope of the invention(s) presently or hereafter claimed.

Further Information about Technical Background to this Application

The disclosures of the Japanese Patent Application including specification, drawings and claims are incorporated herein by references on their entirety: Japanese Patent Application No. 2017-208492 filed Oct. 27, 2017.

The invention claimed is:

1. An active noise control device that reduces noise inside a cabin of a car, the active noise control device comprising:

a reference signal input unit that receives a reference signal having correlation with the noise;

an adaptive filter unit that generates a canceling signal by applying an adaptive filter to the reference signal received;

a canceling signal output unit that receives the canceling signal generated;

an error signal input unit that receives an error signal corresponding to a residual sound resulting from interference between the noise and a canceling sound emitted from a canceling sound source according to the canceling signal;

a simulated acoustic transfer characteristic filter unit that generates a filtered reference signal by adjusting the reference signal using simulated transfer characteristics which simulate acoustic transfer characteristics from the canceling signal output unit to the error signal input unit;

a filter coefficient updater that sequentially updates a coefficient of the adaptive filter using the error signal and the filtered reference signal generated;

a controller that decreases a signal level of the canceling signal when a signal level of the reference signal received is lower than a threshold; and a threshold controller that changes the threshold based on at least one of a signal level of the error signal and information on the car.

2. The active noise control device according to claim 1, wherein the threshold controller decreases the threshold with increase in the signal level of the error signal.

3. The active noise control device according to claim 1, wherein the information on the car is information indicating a driving state of the car.

4. The active noise control device according to claim 3, wherein the information indicating the driving state of the car is information indicating a speed of the car, and the threshold controller decreases the threshold with increase in the speed of the car.

5. The active noise control device according to claim 3, wherein the information indicating the driving state of the car is information indicating a state of an engine of the car, and the threshold controller decreases the threshold during rotation of the engine to less than a threshold during non-rotation of the engine.

6. The active noise control device according to claim 1, wherein the information on the car is information indicating a state of equipment in the car.

7. The active noise control device according to claim 6, wherein the information indicating the state of the equipment in the car is information indicating a state of an air conditioner in the car, and the threshold controller decreases the threshold with increase in a fan speed of the air conditioner.

8. The active noise control device according to claim 1, wherein when the signal level of the reference signal received is lower than the threshold, the controller decreases the signal level of the canceling signal to stop emission of the canceling sound, and causes the filter coefficient updates to stop updating of the coefficient of the adaptive filter.

9. The active noise control device according to claim 1, wherein the controller further performs control to decrease the signal level of the canceling signal when a first parameter included in the information on the car is lower than a threshold.

10. An active noise control device that reduces noise inside a cabin of a car, the active noise control device comprising:

a reference signal input unit that receives a reference signal having correlation with the noise;

an adaptive filter unit that generates a canceling signal by applying an adaptive filter to the reference signal received;

a canceling signal output unit that receives the canceling signal generated;

an error signal input unit that receives an error signal corresponding to a residual sound resulting from interference between the noise and a canceling sound emitted from a canceling sound source according to the canceling signal;

a simulated acoustic transfer characteristic filter unit that generates a filtered reference signal by adjusting the reference signal using simulated transfer characteristics which simulate acoustic transfer characteristics from the canceling signal output unit to the error signal input unit;

a filter coefficient updater that sequentially updates a coefficient of the adaptive filter using the error signal and the filtered reference signal generated;

a car information input unit that receives information on the car;

a controller that decreases a signal level of the canceling signal when a first parameter included in the information on the car is lower than a threshold; and a threshold controller that changes the threshold based on at least one of a signal level of the error signal and a second parameter included in the information on the car, the second parameter being different from the first parameter.

11. The active noise control device according to claim 10, wherein the threshold controller decreases the threshold with increase in the signal level of the error signal.

12. The active noise control device according to claim 10, wherein the first parameter indicates a speed of the car, the second parameter indicates a state of an engine of the car, the controller decreases the signal level of the canceling signal when the speed of the car is lower than the threshold, and the threshold controller decreases the threshold with increase in a rotation speed of the engine.

13. The active noise control device according to claim 10, wherein the first parameter indicates a speed of the car, the second parameter indicates a state of an air conditioner in the car, the controller decreases the signal level of the canceling signal when the speed of the car is lower than the threshold, and the threshold controller decreases the threshold with increase in a fan speed of the air conditioner.

14. The active noise control device according to claim 10, wherein when the first parameter is lower than the threshold, the controller decreases the signal level of the canceling signal to stop emission of the canceling sound, and causes the filter coefficient updater to stop updating of the coefficient of the adaptive filter.

15. The active noise control device according to claim 10, wherein the controller further performs control to decrease the signal level of the canceling signal when a signal level of the reference signal received is lower than a threshold.

16. A car, comprising:

the active noise control device according to claim 1; and the canceling sound source.

17. An active noise control method for reducing noise inside a cabin of a car, the active noise control method comprising:

generating a canceling signal by applying an adaptive filter to a reference signal having correlation with the noise;

generating a filtered reference signal by adjusting the reference signal using simulated transfer characteristics which simulate acoustic transfer characteristics from a canceling signal output unit to an error signal input unit, the canceling signal output unit receiving the canceling signal, the error signal input unit receiving an error signal corresponding to a residual sound resulting from interference between the noise and a canceling sound emitted from a canceling sound source according to the canceling signal generated;

sequentially updating a coefficient of the adaptive filter using the error signal and the filtered reference signal generated;

decreasing a signal level of the canceling signal when a signal level of the reference signal received is lower than a threshold; and changing the threshold based on at least one of a signal level of the error signal and information on the car.

18. An active noise control method for reducing noise inside a cabin of a car, the active noise control method comprising:

generating a canceling signal by applying an adaptive filter to a reference signal having correlation with the noise;

generating a filtered reference signal by adjusting the reference signal using simulated transfer characteristics which simulate acoustic transfer characteristics from a canceling signal output unit to an error signal input unit, the canceling signal output unit receiving the canceling signal, the error signal input unit receiving an error signal corresponding to a residual sound resulting from interference between the noise and a canceling sound emitted from a canceling sound source according to the canceling signal generated;

sequentially updating a coefficient of the adaptive filter using the error signal and the filtered reference signal generated;

decreasing a signal level of the canceling signal when a first parameter included in information on the car is lower than a threshold; and changing the threshold based on at least one of a signal level of the error signal and a second parameter included in the information on the car, the second parameter being different from the first parameter.

* * * * *